United States Patent [19]

Benthin

[11] 4,155,961
[45] May 22, 1979

[54] RESPIRATORY AIR HUMIDIFIER

[75] Inventor: Frank Benthin, Lübeck, Fed. Rep. of Germany

[73] Assignee: Dragerwerk Aktiengesellschaft, Fed. Rep. of Germany

[21] Appl. No.: 868,754

[22] Filed: Jan. 12, 1978

[30] Foreign Application Priority Data

Jan. 31, 1977 [DE] Fed. Rep. of Germany ....... 2703892

[51] Int. Cl.² .................. B01F 3/04; A61M 15/00
[52] U.S. Cl. .................................. 261/104; 128/186; 261/DIG. 65
[58] Field of Search ............. 261/104, 107, DIG. 11, 261/DIG. 65, 153, 154; 165/60, 172, 175, 176; 128/185–188, 191 R, 192–194, 205, 212; 210/321 R, 321 B; 159/DIG. 15, DIG. 27, DIG. 28

[56] References Cited

U.S. PATENT DOCUMENTS

| | | | |
|---|---|---|---|
| 3,007,679 | 11/1961 | Byerley et al. | 165/176 |
| 3,228,877 | 1/1966 | Mahon | 210/321 B X |
| 3,403,531 | 10/1968 | Oesterheld | 261/DIG. 11 |
| 3,702,658 | 11/1972 | McNamara et al. | 210/321 R |
| 3,871,373 | 3/1975 | Jackson | 261/104 X |
| 3,953,334 | 4/1976 | Brun et al. | 210/321 R |
| 4,010,748 | 3/1977 | Dobritz | 261/DIG. 65 |

Primary Examiner—Richard L. Chiesa
Attorney, Agent, or Firm—McGlew and Tuttle

[57] ABSTRACT

A respiratory air humidifier comprises a housing having a flow passage therethrough for the flow of respirator air with a respirator air inlet at one end of the flow passage and a respirator air outlet at the other end of the passage. A plurality of U-shape tubules are disposed in the flow passage and they have walls made of a material permeable to water vapor but impermeable to water. A tubule holder plate closes the flow passage and it is provided with a plurality of bores therethrough of a number corresponding to the tubules located at two spaced locations and into which extend the respective ends of the tubules which are sealed at these ends to the tubular holder plate. A water inlet conduit extends into the inlet of the flow passage and connects the respective inlet end of the tubules, and a water discharge conduit extends out of the flow passage inlet for the discharge of the water from the outlet end of the tubules. The construction includes respective air flow conduits connected through the holder plate and having perforations or air openings along their length which are directed over the surfaces of the tubules so as to pickup the water vapor which advances through the tubular walls in order to humidify the respiratory air.

6 Claims, 3 Drawing Figures

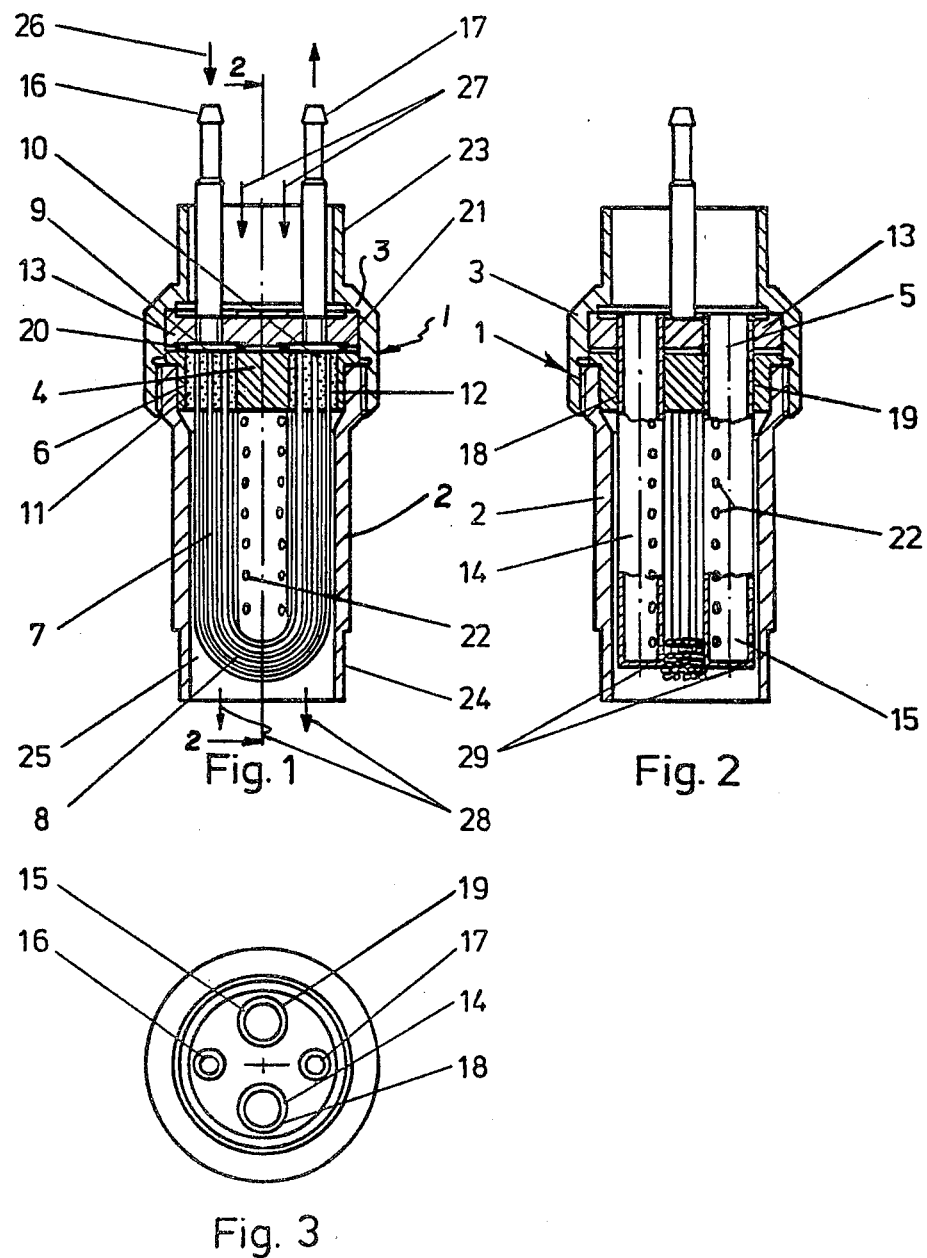

RESPIRATORY AIR HUMIDIFIER

FIELD AND BACKGROUND OF THE INVENTION

This invention relates in general to the construction of humidifiers and, in particular, to a new and useful respiratory air humidifier having a plurality of tubules through which water is passed with walls of a material which is permeable to water vapor but impermeable to water.

DESCRIPTION OF THE PRIOR ART

The present invention relates particularly to respirators and is particularly useful in respect to artificial respirators which are useable for the spontaneous breathing of tracheotomized patients in which the air is not inhaled through the neck, nose and throat space, but directly into the bronchi. Because the neck, nose and throat space is untouched by the inhaled air, the air cannot be sufficiently warmed and moistened. The result is a drying-out of the breathing passages and this impairs the function of the flimmer epithelium.

In order to prevent the drying-out of the breathing passages, a known type of inhaled-air humidifier is used. Its purpose is to warm up the inhaled air if possible to body temperature and, in the process, to raise the air to a maximal 100% of relative humidity.

A known inhaled-air humidifier is a tank for respirator devices which contains an evaporation surface. On one side, warm water is admitted, and the other side is in contact with the breathing gas to be moistened. The evaporation surface is produced by a film which is made of a water-impermeable, but water vapor permeable, material. To increase the evaporation surface, it can be shaped as a star in the tank. The evaporated water with which the breathing gas is moistened, together with the inhaled-air current carried past the gas-admitted side of the evaporation surface, gets to the patient. The non-evaporated water is recirculated to the supply tank.

Because of such an arrangement, even as a star-shaped configuration, the evaporation surface requires a large evaporating space. Thus, the entire inhaled-air humidifier increases in size accordingly. The handling of the evaporating surface for cleaning and the required disinfection is difficult and must be carried out very carefully. See German Pat. No. 2,430,875.

Also known are inhaled-air humidifiers which contain two water hoses which are moved back and forth in the inhaled air hose or they feed the inhaled air through a breathing air hose having a plurality of bent-off sections in a water supply. In the first case, it is the water hose carried in the air hose, and in the second case, the water tank carried air hose, which is made of a material which is water-impermeable but water vapor permeable.

Even these known inhaled-air humidifiers have large space requirements for accommodating a sufficiently large evaporation surface. Its removal for cleaning and disinfecting purposes is difficult, if not impossible. See U.S. Pat. No. 3,871,373.

SUMMARY OF THE INVENTION

In accordance with the present invention, there is provided a humidifier for respirator air which includes a tubular member defining a flow passage for the respiratory air having an inlet at one end and an outlet at the opposite end for the circulation of the respiratory air therethrough.

The interior of the housing is closed by a holder plate having a plurality of bores into which are engaged respective ends of a bundle of tubules of U-shape configuration. The inlet ends of the tubules are connected through the holder plate to a water inlet conduit connection and the outlet ends are connected through the holder plate to a water discharge connection. The respiratory air is circulated from the passage through conduits which extend through the holder plate and which have a plurality of openings along their lengths which permit the direction of the air flow into the tubular bundle of the tubules. Because the tubules are made of a substance which permits the passage of water vapor therethrough, but not water, the air which is circulated through the cylindrical housing is moistened as it moves past and over the tubules.

Accordingly, an object of the invention is to provide an inhaled-air humidifier which is of a relatively small size so as to avoid condensation, and which permits a construction in which it can be inserted near the patient in the inhaled-air supply and in which the inhaled-air carrying parts are easy to clean and to disinfect.

A further object of the invention is to provide a respirator air humidifier which includes a passage therethrough for the flow of the air to be humidified and with a bundle of tubules disposed across the passage through which water is circulated and which are made of a material which is permeable to water vapors so that the air flowing through the passage is moistened.

Another object of the invention is the provision of a humidifier which is capable of being built to very small dimensions and which facilitates the placing of the construction close to the patient and which may be operated without a condensation of the inhaled air through the use of hollow fibers which allows for a large evaporation surface to be accommodated in a small space.

A further object of the invention is to provide a humidifier in which the various evaporation and flow components are constructed to fit into a small size tubular member and in which the components may be easily separated for simple handling and cleaning. The construction includes inexpensive synthetic parts which makes it possible to even exchange them after each use.

A further object of the invention is to provide a humidifier for respiratory air which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which a preferred embodiment of the invention is illustrated.

BRIEF DESCRIPTION OF THE DRAWING

In the drawing:

FIG. 1 is a transverse sectional view of a humidifier constructed in accordance with the invention;

FIG. 2 is a section taken along the line 2—2 of FIG. 1; and

FIG. 3 is a top plan view of the device shown in FIG. 1.

DESCRIPTION OF THE PREFERRED EMBODIMENT

Referring to the drawing in particular, the invention embodied therein in FIG. 1, comprises a humidifier for respiratory air which includes a housing, generally designated 1, having a lower cylindrical housing part 2 and an upper cylindrical housing part or cover 3. Each end of housing 1 is opened for the passage of air through an inlet end in the direction of the arrows 27 out through a discharge end in the direction of the arrows 28.

In accordance with the invention, the respiratory air which flows in the inlet and out the outlet is enriched or moistened with water which is directed in the direction of the arrow 26 through an inlet conduit connection 16 into a carrier plate 13 of a plate holder including a round body or plate member 6. The inlet conduit 16 communicates at its inner end with inlet ends of a plurality of U-shaped fiber tubules 7 which have their inlets engaged in a plurality of respective openings 11 of the holder 6 and have outlet ends which engage through a plurality of openings 12 at a spaced location from the openings 11. The inlet ends of the tubules at the location 9 connect to the inlet conduit 16 and the outlet ends 10 connect to a discharge pipe or conduit 17 which also extends out of the inlet end of the housing 1. The respiratory air is directed through inlet air tube 14 and through perforations or openings 22 at spaced locations along the length of inlet tube 14 on the downstream side of the header plate 4 and also through inlet tube 15 for similar flow through openings 22 which are oriented against the bundle of tubules 7 so as to direct the air flow over and through the tubes and then out the outlet of the conduit in the direction of the arrows 28.

The holder plate 6 is part of an evaporating unit, generally designated 4. Unit 4 also provides a means for connecting the air flow unit, generally designated 5.

In accordance with a feature of the invention, the bundle of U-shaped tubules 7 are made up of indivdually U-shaped bent hollow fiber tubes 8. The tubes are arranged parallel to each other and are made of a material which is impermeable to water, but permeable to water vapor. The wall thickness of each individual tubule 8 is about 15 microns. The diameter of the tubules is less than 300 microns. The respective inlet and outlet ends 9 and 10 of the hollow fiber tubes 8 are open to the front and they are tight-sealed in perforations 11 and 12 by a casting compound.

The flow part 5 comprises the carrier plate 13 with both air tubes 14 and 15 extending therethrough and both relatively rectangular-angled water connections 16 and 17. In addition, the holder plate 6 contains both bores 18 and 19 through which both the air hoses 14 and 15 are carried.

Packings 20 and 21 seal off the holder plate 6 and the carrier plate 13 from each other. This separates the air feed from the water feed. Air tubes 14 and 15 have the openings 22 which are vectored or shaped so that the air is directed against the individual fiber tubules 8 and flows through these tubules due to the closed bottom 29 and then outwardly from housing 1 in the direction of the arrows 28.

With the invention, housing 1 may be inserted in the respiratory line near the patient with respective sleeve portions 23 and 24 at each end connected directly into the respirator circulating line connection (not shown). Water from the direction 26 for moistening the inhaled air is diverted to or from water connections 16 and 17 via connecting lines, which are not shown. The respiratory air which flows through the housing 1 is raised to the desired temperature by preheated water without any additional required heating. The water flows via the supply water connection 16 through the bores of the hollow fibers 8 and then flows off again through the discharge connection 17.

The inhaled air to be moistened flows in the direction 27 through the sleeve 23 in cover part 3 and through the air openings 22 of the air hoses 14 and 15 and then into the space 25 of the housing part 2 in which the bundle 7 is located. The air then flows around the exterior surfaces of the tubules 8 and picks up moisture in the process. The moistened inhaled-air leaves the inhaled-air humidifier in the direction of the arrows 28 for the breathing air connection which is engaged over the sleeve 24.

While a specific embodiment of the invention has been shown and described in detail to illustrate the application of the principles of the invention, it will be understood that the invention may be embodied otherwise without departing from such principles.

What is claimed is:

1. A respirator air humidifier, comprising a housing having a flow passage therethrough for the flow of respirator air with a respirator air inlet at one end of said flow passage and a respirator air outlet at the other end of said flow passage, a plurality of U-shaped tubules disposed in said flow passage having walls made of a material permeable to water vapor but impermeable to water, a tubule-holder plate closing said flow passage and having a plurality of bores therethrough of a number corresponding to said tubules located at two spaced apart locations, said tubules having respective inlet and outlet ends extending into respective bores at respective locations of said holder plate and being sealed to said plate, water inlet and outlet conduit means extending into said flow passage and connecting the respective inlet and outlet ends of said tubules for circulating water therethrough, and air inlet and outlet conduit means extending through said tubular holder plate for circulating the respiratory air from the inlet of said flow passage over the surfaces of said tubules between said respiratory air inlet and said respiratory air outlet so as to pick off water vapor passed through said tubules to humidify said respiratory air.

2. A respirator air humidifier, as claimed in claim 1, wherein said holder plate includes at least a portion adjacent the inlet and outlet ends of said tubules of a plastic bonding material.

3. A respirator air humidifier, as claimed in claim 1, including a carrier plate directly adjacent said holder plate, said water inlet and outlet conduit means comprising a separate water inlet conduit and a separate water outlet conduit connected to said carrier plate, and packing means disposed between said carrier plate and said holder plate permitting communication of the end of respective inlet conduits with the inlet ends of said tubules and the end of the respective outlet conduits with the outlet ends of said tubules.

4. A respirator air humidifier, as claimed in claim 1, wherein said air inlet and outlet conduit means comprises two air inlet conduits extending through said carrier plate and said holder plate and having communication with one end with the air flow passage and being closed at the opposite discharge end of said air flow passage and being provided with a plurality of openings along the length thereof through which the air passes over said tubules.

5. A respirator air humidifier, as claimed in claim 1, wherein said tubules have wall thicknesses of about 15 microns and have inner diameters of less than 300 microns.

6. A respirator air humidifier, as claimed in claim 1, wherein said respirator housing includes a cylindrical housing member and a cover member secured to said cylindrical housing member, said holder plate being disposed between said cover and said housing member to permit separation of said cover and said housing members and removal of said holder plate with said tubules.

* * * * *